United States Patent [19]

Dory

[11] Patent Number: 4,617,931
[45] Date of Patent: Oct. 21, 1986

[54] ULTRASONIC PULSE APPARATUS FOR DESTROYING CALCULUSES

[76] Inventor: Jacques Dory, 991, rue des Molveaux, 77450 Coupvray Esblay, France

[21] Appl. No.: 674,889
[22] Filed: Nov. 26, 1984

[30] Foreign Application Priority Data

Dec. 14, 1983 [FR] France ............... 83 20041

[51] Int. Cl.$^4$ ............................................. A61B 17/00
[52] U.S. Cl. ..................................... 128/328; 128/304
[58] Field of Search ................... 128/304, 328, 24 R

[56] References Cited

U.S. PATENT DOCUMENTS

| | | | |
|---|---|---|---|
| 4,046,149 | 9/1977 | Komiya | 128/328 |
| 4,311,147 | 1/1982 | Hausler | 128/328 |
| 4,474,180 | 10/1984 | Angulo | 128/328 |
| 4,486,680 | 12/1984 | Bonnet et al. | 128/328 |

Primary Examiner—Robert Peshock
Assistant Examiner—Wenceslao J. Contreras
Attorney, Agent, or Firm—William A. Drucker

[57] ABSTRACT

A lithotrite comprising means for generating shock waves concentrated in a focal region and means for locating the position of said focal region, said generating means comprising an ultrasonic pulse generator comprising a main piezoelectric transducer whose active surface is a spherical cap, whereas said locating means comprise an echography device comprising an auxiliary pulse generator associated with an auxiliary transducer fixed to said spherical cap.

7 Claims, 4 Drawing Figures

ULTRASONIC PULSE APPARATUS FOR DESTROYING CALCULUSES

BACKGROUND OF THE INVENTION

1. Field of the Invention

The invention relates to a lithotrite which may be constructed for a lower cost than those using shock wave generation by means of a spark gap and location of the calculus by radioscopy and having, with respect to these known apparatus, different substantial advantages and in particular more accurate and reliable location of the calculus and simplified use.

2. Description of the Prior Art

In a known apparatus, shock waves are generated by electric discharges effected at the focal point of an elliptic reflector and are focused at the second focal point of the ellipse. The energy of the focal spot will only be sufficient for destroying an infra-renal calculus (pressures of the order of $10^8$ pascal are required) if the transmission takes place in a liquid (water) perfectly free of gas, which is an important restriction of use. This process further requires the expensive electrodes of the spark gap to be changed at each treatment or even during treatment. The focal spot produced is relatively large. Finally, location by means of two orthogonal x ray beams is complex and subject to errors.

SUMMARY OF THE INVENTION

The invention overcomes these disadvantages by generating shock waves by means of an ultrasonic pulse generator in which the active surface of the transducer is spherical. The shock waves emitted are thus focused directly at the center of the spherical emitting surface.

In a preferred embodiment, location of the calculus is achieved by using an echography device comprising an auxiliary ultrasonic generator whose transducer is fixed to said spherical surface. During movement of the main transducer for bringing the focal spot into the desired region of the calculus, the auxiliary transducer thus supplies at all times an image of the calculus and of the focal spot, which allows the desired localization to be achieved easily and accurately.

According to another feature of the invention, the apparatus comprises means for causing the main transducer to emit, during the intervals between the main pulses, control pulses having a substantially reduced power, at the same rate as the pulses emitted by the auxiliary transducer, the corresponding echos received by the auxiliary transducer being processed for controlling the localization and the distribution of the energy of the main pulses.

BRIEF DESCRIPTION OF THE DRAWINGS

Other features as well as the advantages of the invention will be clear from the following description.

In the accompanying drawings.

DESCRIPTION OF THE PREFERRED EMBODIMENT

Figure 1:
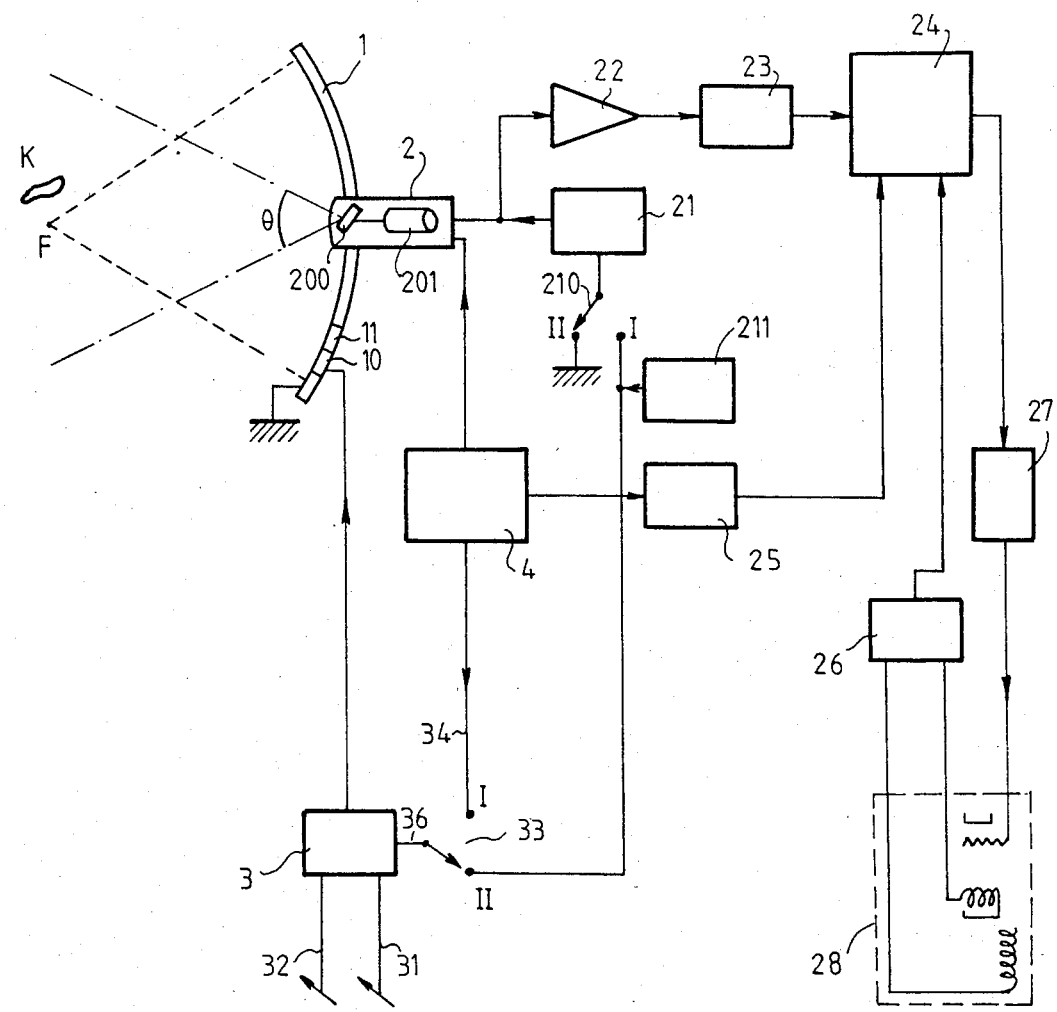
FIG. 1 is the general diagram of an apparatus according to a preferred embodiment of the invention.
Figure 2:
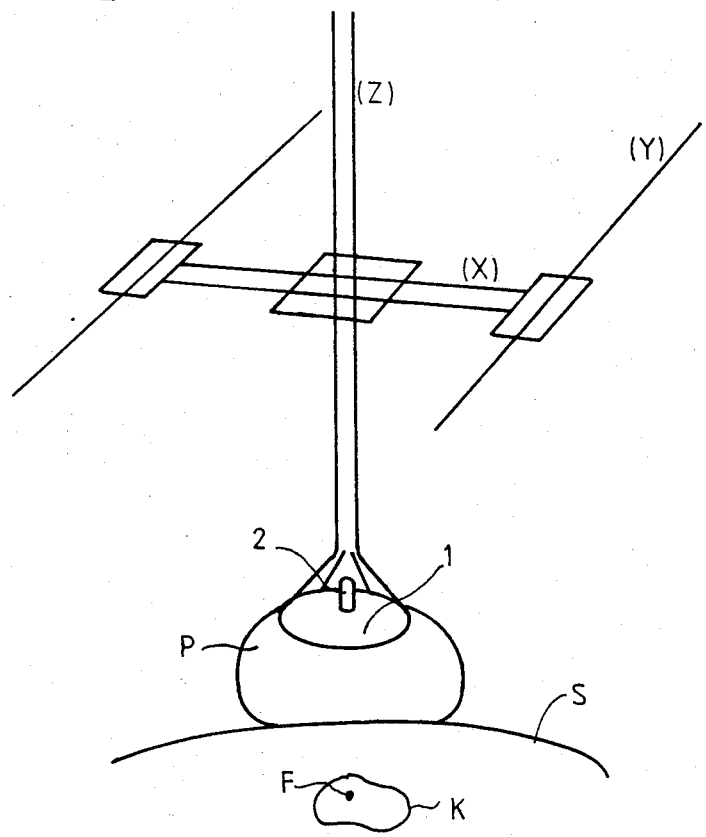
FIG. 2 shows schematically, in perspective, the main transducer and its mobile support device.
Figure 4:
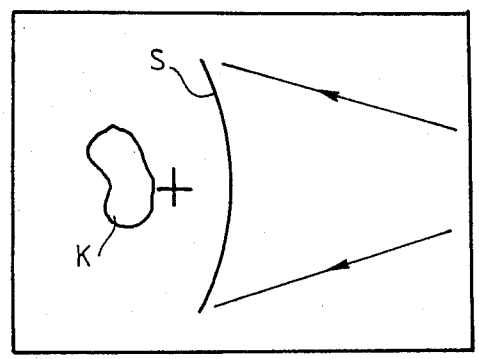
FIG. 4 shows the image obtained on the display screen which the apparatus comprises.

In FIG. 2 is shown a transducer 1 in the form of a spherical skull cap supported by a device allowing it to move along three orthogonal axes X, Y and Z. This device has been shown schematically, construction thereof being within the scope of a man skilled in the art. Along the axis of the spherical skull cap is disposed an auxiliary transducer 2 of a general cylindrical shape, which passes through skull cap 1 and is fixed thereto. Water pocket P is interposed between the skull cap 1 and surface S of the body of the patient, this latter being assumed lying down on a horizontal surface. Skull cap 1 is for example 200 to 300 mm in diameter and is formed from a large number (300 or 400) of piezoelectric elements 10, 11, etc ... (FIG. 1) isolated from each other and juxtaposed so as to form a mosaic. These elements are metallized on both their faces, one of the metallizations being connected to ground and the other to energization connections through an emitter 3.

Figure 3:
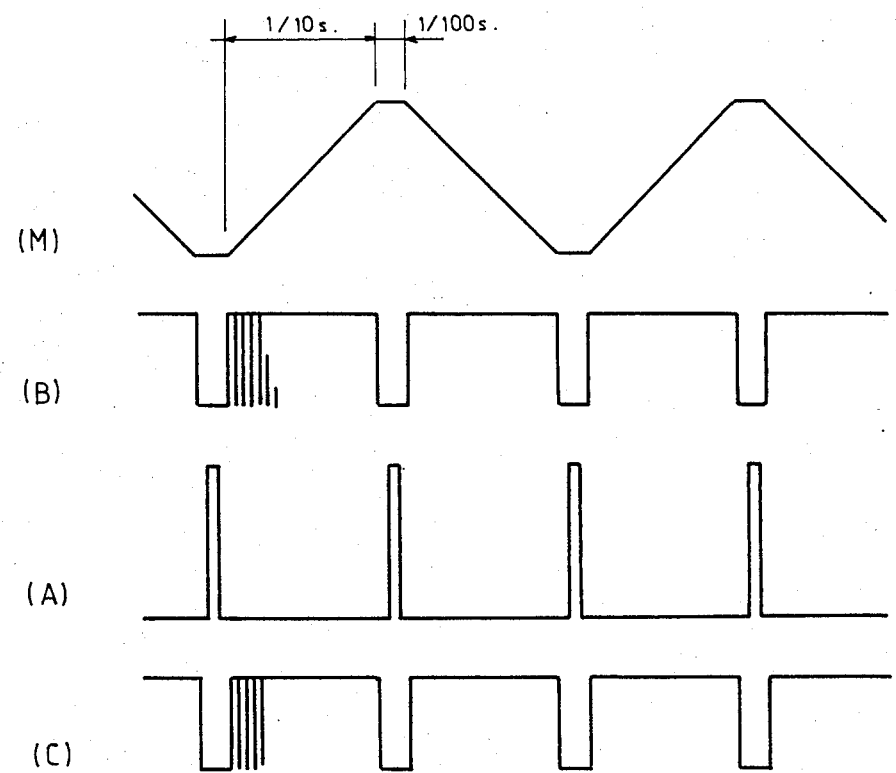
FIG. 3 shows the wave forms at different points of the circuits of the apparatus.

This latter supplies an electric signal A (FIG. 3) formed of high frequency (500 KHz for example) pulse bursts of short duration (for example 1 microsecond). Each burst will for example comprise a number of pulses between 1 and 10 and these pulses correspond to a very high peak power (of the order of 100 Kw for example). Such power may be obtained by means of a pulse emitter using well known technologies, either with power transistors, or with thyristors. All the elements may be energized in parallel or groups of elements placed in series may be energized.

An input 31 of emitter 3 symbolizes adjustment of the power emitted and an input 32 adjustment of the pulse shape. These adjustments allow the shape of the signal produced at the level of the focal spot, in the center F of the sphere, to be controlled. This sphere may, with this technique, be very small (diameter of two or three millimeters for example) and may have a strictly fixed position for a given position of the transducer.

In FIG. 1, it can be seen that the auxiliary transducer 2 is itself connected, on the one hand, to an electric pulse emitter 21, and on the other hand to a reception amplifier 22 followed by an analog-digital converter 23 itself followed by a memory 24. The emitter 21 is synchronized by a pulse generator 211 which supplies 256 pulses (square wave B, FIG. 3) in a time (1/10 of a second for example) less than the pulse period A. This time corresponds to the time required for a complete sweep of a predetermined angular sector $\theta$ (FIG. 1) by the beam emitted by the transducer 2, thus forming in the sweep plane an image of calculus K.

The transducer 2 is advantageously of the type described in French patent application No. 80 16717 filed on the July 29, 1980: Echography probe with sectorial sweep comprising two coupling liquids and No. 80 16718 filed on the July 29, 1980: Echography probe with mechanical sectorial sweep, that is to say that it comprises an oscillating piezoelectric element 200 controlled by a motor 201, itself controlled by an electronic circuit which has been symbolized by a rectangle 4. This electronic circuit supplies signals (M, FIG. 3) for controlling the motor 201 housed in the case of transducer 2 and is adapted so that a complete oscillation of the motor corresponds to the above defined duration required for formation of an image (1/10 sec). A short predetermined time interval after the end of square wave B, switch 33 being assumed in position I, circuit 4 sends out a 1/100 second pulse, for example, transmitted to the input 36 of emitter 3 for initiating the emission of a pulse burst A. During this initiating pulse, the oscillation element 200 remains immobile at the end of the sweep so that the probe does not receive corresponding echos.

It is possible to omit the connection between generator 211 and emitter 21 by putting switch 210 in position II. In this operating mode, emitter 21 is no longer in service and transducer 2 is only used for reception. On the other hand, with switch 33 assumed to be in position II at the same time as switch 210 (coupling between these two switches has not been shown), the emitter 3 is then synchronized by generator 211, so that it emits pulses C (FIG. 3) at the same rate as the above mentioned pulses B.

Emitter 3 thus energizes, when the switches are in position II, transducer 1 with a signal C formed of sequences of 256 pulses for example. The corrsponding echos are recieved by transducer 2, so that an image of the zone of concentration of the energy then emitted by transducer 1 is obtained, as will be explained further on.

Pulses B emitted by emitter 21 and pulses C emitted by emitter 3 are of low power (a few watts peak). The power of emitter 21 is adjustable and that of emitter 3 is, at the time of switching switch 33 to position II, considerably reduced for example by a substantial reduction of the supply voltage for the emitter 3, which reduction is controlled by said switching in a way known per se and not shown. The signals received at 22, whatever their nature, are, after analog-digital conversion in 23, stored line by line in memory 24, a writing addressing device 25, controlled by circuit 4, causing the respective deflection angles of the beam emitted and/or received by transducer 2 to correspond with the respective lines of the memory. A device 26 for rapid reading of the memory energizes the X and Y deflection coils of cathode ray tube 28, so the brilliancy control electrode receives the corresponding contents from memory 24, transformed into an analog signal by a digital-analog converter 27.

The practical construction of all the circuits described and shown is within the scope of a man skilled in the art.

The apparatus which has just been described operates in the following way:

As was mentioned above, in normal operation, the switches are in position I and ultrasonic pulses corresponding to pulses A are generated by transducer 1 and focused at the center F of the sphere. During each square wave B, the sectorial sweep echography device formed by the transducer, the auxiliary emitter and the reception, processing and display means 22 to 27, displays on the screen an image of the zone swept, so of the kidney and of the calculus K.

Furthermore, the display device is adapted, in a way known per se, for materializing on the screen of the cathode ray tube (for example by a cross) the theoretical position of a focal spot in the sectional plane shown, which plane passes through the axis of symmetry of transducer 1. (It is a question of echography of type B). The operator begins by moving transducer 1 along X, until the calculus appears clearly on the screen, then he moves it along Y and Z until the cross coincides with the central region of the calculus image At that time, the switches may be placed in position II; the region of the focal spot is then made visible on the screen, with a luminosity proportional to the corresponding concentration of energy. Thus a representation is obtained of what the distribution of the energy of the shock wave will be during firing, which allows the adjustments to be checked and perfected.

It is clear that the apparatus described allows the change in the calculus after each firing to be checked. It goes without saying that it may undergo different modifications and even be implemented in different ways without departing from the scope and spirit of the invention.

What is claimed is:

1. A lithotrite for contact free pulsed wave disintegration of calculi, said lithotrite comprising:
    (i) high power ultrasonic pulse generator means;
    (ii) piezoelectric transducer means having a spherical transmissive surface portion, in contact with a water-containing enclosure and adapted to focus the disintegrating waves at a focal spot substantially located at the center of the said spherical surface, said center being located out of said water-containing enclosure;
    (iii) means connecting the said pulse generator means to said piezoelectric transducer means;
    (iv) image forming means for displaying an image of the said calculus and a representation of the position of the said focal spot; and
    (v) means for displacing the said piezoelectric transducer means to bring the said image and the said representation into coincidence.

2. The lithotrite as claimed in claim 1, wherein the said image forming means comprises auxiliary pulse generator means and auxiliary transducer means integrally coupled to said piezoelectric transducer means and normally connected to said auxiliary pulse generator means.

3. The lithotrite as claimed in claim 2, wherein the said image forming means further comprise means for effecting sectorial sweeps of the ultrasonic pulsed wave beam generated by the said auxiliary transducer means during time intervals contained within the time intervals between the respective ultrasonic pulses generated by the said piezoelectric transducer means, said sectorial sweeps being effected in a plan which passes through an axis of symmetry of said transmissive surface portion.

4. The lithotrite as claimed in claim 1, wherein the said piezoelectric transducer means are formed by a mosaic of piezoelectric elements isolated from each other.

5. The lithotrite as claimed in claim 1, wherein the said means for displacing the piezoelectric transducer means are adapted to control the displacement of said piezoelectric transducer means along three orthogonal axes and said image forming means comprise a cathode ray tube and means for representing, on the screen of said cathode ray tube, the position of the said focal spot in a plan passing through the axis of symmetry of the said piezoelectric transducer means.

6. The lithotrite as claimed in claim 2, said lithotrite further comprising first means for substantially reducing the power output of said high power ultrasonic pulse generator means; second means for synchronizing the pulse frequency of the said high power ultrasonic pulse generator with the pulse frequency of said auxiliary pulse generator means, and switching means for putting said first and second means into service, while disconnecting the said auxiliary transducer.

7. The lithotrite as claimed in claim 6, wherein said first means comprise means for substantially reducing the supply voltage of said high power ultrasonic pulse generator.

* * * * *

REEXAMINATION CERTIFICATE (895th)
United States Patent [19]
Dory

[11] B1 4,617,931

[45] Certificate Issued  Jul. 12, 1988

[54] ULTRASONIC PULSE APPARATUS FOR DESTROYING CALCULUSES

[76] Inventor: Jacques Dory, [9] 91, rue des Molveaux, 77450 Coupvray, Esblay, France

Reexamination Request:
No. 90/001,184, Mar. 2, 1987

Reexamination Certificate for:
Patent No.: 4,617,931
Issued: Oct. 21, 1986
Appl. No.: 674,889
Filed: Nov. 26, 1984

[30] Foreign Application Priority Data

Dec. 14, 1983 [FR] France ............... 83 20041

[51] Int. Cl.⁴ ................ A61B 17/22; A61B 17/20
[52] U.S. Cl. ................... 128/328; 128/24 A
[58] Field of Search ........................... 128/328

[56] References Cited

U.S. PATENT DOCUMENTS

| | | | |
|---|---|---|---|
| 3,237,623 | 3/1966 | Gordon | 128/24 |
| 3,735,755 | 5/1973 | Eggleton et al. | 128/24 A |
| 3,756,071 | 9/1973 | Dory | 73/67.8 |
| 4,005,258 | 1/1977 | Dory | 358/112 |
| 4,281,661 | 8/1981 | Dory | 128/660 |
| 4,340,944 | 7/1982 | Dory | 367/96 |
| 4,418,698 | 12/1983 | Dory | 128/660 |
| 4,484,569 | 11/1984 | Driller et al. | 128/660 |
| 4,526,168 | 7/1985 | Hassler et al. | 128/303 R |

FOREIGN PATENT DOCUMENTS

| | | | |
|---|---|---|---|
| 2722252 | 11/1978 | Fed. Rep. of Germany | 128/328 |
| 3122056 | 12/1982 | Fed. Rep. of Germany | 128/328 |
| 3142639 | 5/1983 | Fed. Rep. of Germany | 128/328 |
| 2113099 | 8/1983 | United Kingdom | |
| 602180 | 4/1978 | U.S.S.R. | 128/328 |

OTHER PUBLICATIONS

*Generating High-Energy Ultrasound Pulses with Focusing Piezo Transducers*, Reidlinger et al. (1982).
*Sources of High Intensity Ultrasound*, edited by L. D. Rozenberg, vol. 1, Plenum Press, N.Y. (1969).
*Applications of Therapeutic Ultrasound in Ophthamology*, Lizzi et al., Progress in Medical Ultrasound, vol. 2 (1981).
*Precision High Intensity Focusing Ultrasonic Machines for Surgery*, Fry, Am. Jour. of Physical Medicine, vol. 37, No. 3 (6-1978).
*Ultrasound: Its Application in Medicine and Biology*, edited by Fry (1978).
*Therapeutic Ultrasound in the Production of Ocular Lesions*, Lizzi et al., Am. Jour. of Ophthalmology 86:185-192 (1978).
"Production of Deep Focal Lesions by Focused Ultrasound-Current Status", by P. P. Lele, *Ultrasonics*, Apr. 1967, pp. 105-112.

*Primary Examiner*—Michael H. Thaler

[57] ABSTRACT

A lithotrite comprising means for generating shock waves concentrated in a focal region and means for locating the position of said focal region, said generating means comprising an ultrasonic pulse generator comprising a main piezoelectric transducer whose active surface is a spherical [cap] segment, whereas said locating means comprise an echography device comprising an auxiliary pulse generator associated with an auxiliary transducer fixed to said spherical [cap] segment.

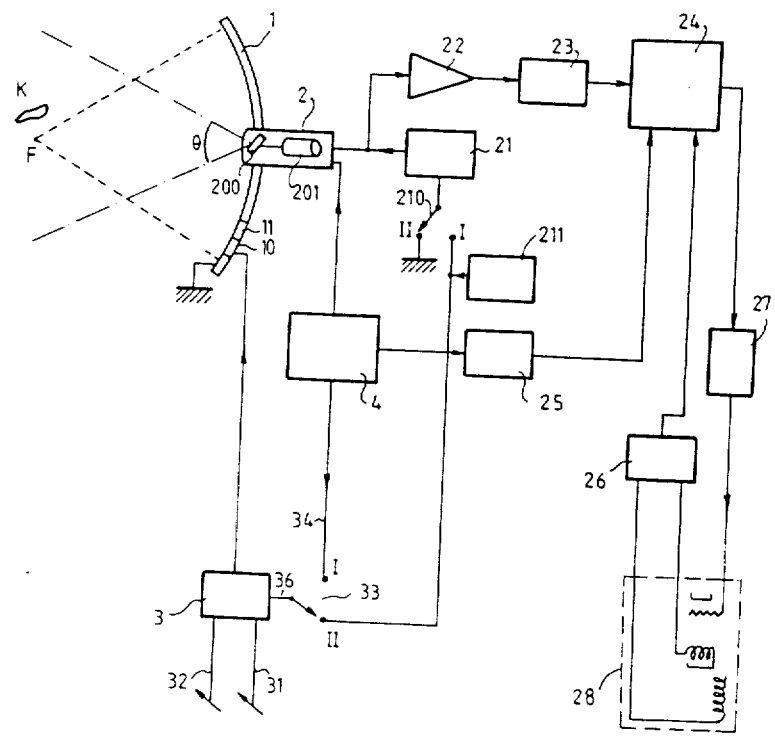

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 4–21:

DESCRIPTION OF THE PREFERRED EMBODIMENT

In FIG. 2 is shown a transducer 1 in the form of a spherical [skull cap] *segment* supported by a device allowing it to move along three orthogonal axes X, Y and Z. This device has been shown schematically, construction thereof being within the scope of a man skilled in the art. Along the axis of the spherical [skull cap] *segment* is disposed an auxiliary transducer 2 of a general cylindrical shape, which passes through [skull cap] *spherical segment* 1 and is fixed thereto. Water pocket P is interposed between the [skull cap] *spherical segment* 1 and surface S of the body of the patient, this latter being assumed lying down on a horizontal surface. [Skull cap] *Spherical segment* 1 is for example 200 to 300 mm in diameter and is formed from a large number (300 to 400) of piezoelectric elements 10, 11, etc. . . . (FIG. 1) isolated from each other and juxtaposed so as to form a mosaic. These elements are metallized on both their faces, one of the metallizations being connected to ground and the other to energization connections through an emitter 3.

Column 2, lines 33–40:

An input 31 of emitter 3 symbolizes adjustment of the power emitted and an input 32 adjustment of the pulse shape. These adjustments allow the shape of the signal produced at the level of the focal spot, in the center F of the sphere, to be controlled. This [sphere] *spot* may, with this technique, be very small (diameter of two or three millimeters for example) and may have a strictly fixed position for a given position of the transducer.

Column 3, lines 46–54:

As was mentioned above, in normal operation, the switches are in position I and ultrasonic pulses corresponding to pulses A are generated by transducer 1 and focused at the center F of the sphere. During each square wave B, the sectorial sweep echography device formed by the transducer, the auxiliary emitter and the reception, processing and display means 22 to 27, displays on the screen an image of the zone swept [, so] of the kidney and of the calculus K.

AS A RESULT OF REEXAMINATION, IT HAS BEEN DETERMINED THAT:

Claim 2 is cancelled.

Claims 1, 3, 5 and 6 are determined to be patentable as amended.

Claims 4 and 7, dependent on an amended claim, are determined to be patentable.

1. A lithotrite for [contact free] *focused* pulsed wave disintegration of calculi, said lithotrite comprising:
   (i) high power ultrasonic pulse generator means;
   (ii) *high power* piezoelectric transducer means *responsive to said generator*, having a spherical transmissive surface portion[,] in contact with a water-containing enclosure [and adapted to focus the] , *for generating a* disintegrating [waves] *pulsed wave beam focused* at a focal spot substantially located [at the center] *along the axis* of [the] said [spherical] surface, said [center] *spot* being located out of said water containing enclosure;
   (iii) means connecting [the] *said* pulse generator means to said piezoelectric transducer means;
   (iv) image forming means for displaying [an image] *real time serial two dimensional images* of [the said] *a* calculus and a *visual* representation of the position of [the] said focal spot, *said image forming means comprising auxiliary pulse generator means; echographic beam auxiliary transmitter-receiver means and scanning means effecting successive sweeps of said echographic beam to form and display serial images of the calculus;* and
   (v) means [for] displacing [the] *said high power* piezoelectric transducer means *and said auxiliary transmitter-receiver means* to bring [the] said [image] *images* and [the] said representation into coincidence.

3. The lithotrite as claimed in claim [2] *1*, wherein [the] said [image forming means further comprise means for effecting] *scanning means effect* sectorial sweeps of the [ultrasonic] *echographic* [pulsed wave] beam [generated by the said auxiliary transducer means] during time intervals [contained within the time intervals] between [the respective] ultrasonic pulses generated by [the] *said high power* piezoelectric transducer means, said sectorial sweeps being effected in a [plan] *plane* which passes through [an] *said* axis [of symmetry] of said transmissive surface portion.

5. The lithotrite as claimed in claim 1, wherein [the] said means for displacing the piezoelectric transducer means [are adapted to control the] *controls* displacement of said [piezoelectric] transducer means along [three] orthogonal axes; [and said image forming means comprise a cathode ray tube] and means [for representing, on the screen of said cathode ray tube,] *displaying a visual representation* [the position] of the *position of* said focal spot in a [plan] *plane* passing through [the] *said* axis of [symmetry of the] said [piezoelectric] transducer means.

6. The lithotrite as claimed in claim [2] *1*, said lithotrite further comprising first means for substantially reducing the power output of said high power ultrasonic pulse generator means, *while the latter is connected to said high power piezoelectric transducer means*; second means for synchronizing the pulse frequency of [the] said high power ultrasonic pulse generator *means* with the pulse frequency of said auxiliary pulse generator means, and switching means for [putting] *placing* said first and second means into service [while disconnecting the said auxiliary transducer] *to display an image of the energy distribution reflected from the region of the focal spot by the high power transducer means at reduced power output*.

* * * * *